United States Patent [19]

Breyer et al.

[11] Patent Number: 4,706,681
[45] Date of Patent: Nov. 17, 1987

[54] CARDIAC ULTRASONICALLY MARKED LEADS AND METHOD FOR USED SAME

[75] Inventors: Branko Breyer; Ivo Cikes; Bozidar Ferek-Petric, all of Zagreb, Yugoslavia

[73] Assignee: Telectronics N.V., Curacao, Netherlands

[21] Appl. No.: 744,375

[22] Filed: Jun. 13, 1985

[30] Foreign Application Priority Data

Jul. 26, 1984 [YU] Yugoslavia .......................... 1328/84

[51] Int. Cl.⁴ .................... A61B 5/04; A61B 10/00; A61N 1/05
[52] U.S. Cl. .................................. 128/642; 128/661; 128/786
[58] Field of Search ................... 128/642, 784–786, 128/419 P, 660–663

[56] References Cited

U.S. PATENT DOCUMENTS

| 3,938,502 | 2/1976 | Bom | 128/661 X |
| 4,319,580 | 3/1982 | Colley et al. | 128/661 |
| 4,409,994 | 10/1983 | Doring | 128/785 |

Primary Examiner—Lee S. Cohen
Attorney, Agent, or Firm—Gottlieb, Rackman & Reisman

[57] ABSTRACT

Cardiac ultrasonically marked leads produced by mounting one or more piezoelectric marker transducers into the leads and connecting the transducers by electrical conductors to appropriate electronic circuits which, upon reception of the scanner ultrasonic signals by the marker transducers, generate appropriate electrical signals which localize unambiguously the marker transducers in an ultrasonic echographic image, thereby permitting guiding of pacing leads and detection of their malfunctions.

4 Claims, 7 Drawing Figures

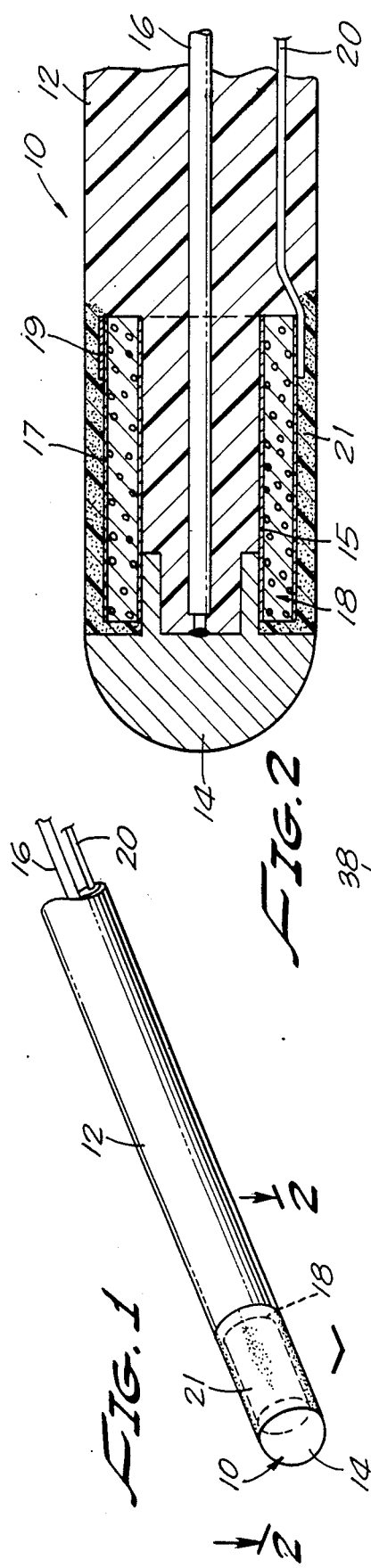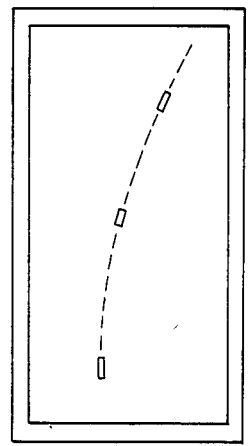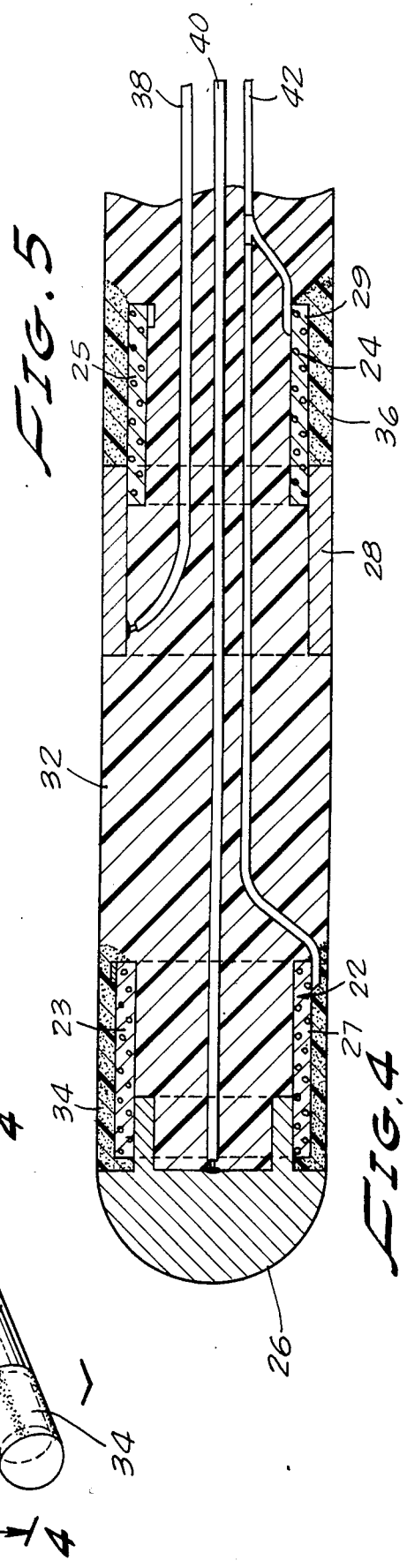

CARDIAC ULTRASONICALLY MARKED LEADS AND METHOD FOR USED SAME

FIELD OF THE INVENTION

This invention relates to ultrasonically echographic guidance and control of cardiac pacing and electrophysiologic study leads that are implanted temporarily or permanently in a person and detection of any malfunction of them.

BACKGROUND AND PRIOR ART

External and implant cardiac pacemakers are widely used in modern medicine to diagnose and treat a broad class of cardiac arrhythmias. Electrical pulses for heart stimulation or other electrotherapy are led to the heart muscle using flexible electrical leads with an active electrode on their tips. By the same means, usually by multipolar leads, the electric signals of the heart are taken to electronic systems for electrophysiologic study procedures.

Presently, the procedures are done using X-ray imaging methods for position and damage control. The disadvantages of X-ray methods are the ionizing radiation hazard and poor imaging of soft tissues, i.e., papillary muscle, interventricular septa, and so forth. Furthermore, a fracture of the lead conductor and of its insulation cannot be well detected by presently known techniques.

Ultrasonic imaging is well suited for soft tissues and presents no X-ray hazard, but has the disadvantage of imaging in one plane - tomographically. Accordingly, the flexible leads can be imaged, but the tip or any other part of interest cannot be positively identified, since the tip in the image can just be the point of the lead which leaves or enters the scanning plane.

SUMMARY OF THE INVENTION

According to the present invention, one or more marker piezoelectric transducers are mounted fixed at one or more points of interest along the leads. Partly using pacing conductors, the transducers are connected to matching electronic circuits. The marker transducers are basically of cylindrical (tubiform) shape of such dimensions as not to impede application of the leads using conventional applicator means. The matching electronic circuits (not shown) use the electrical signals from the marker transducers to produce a mark on the echographic image. The electrical lead conductors are used for cardiac pacing and transmission of electrophysiological signals, as well as for marker transducer signal transmission.

It is, therefore, an object of this invention to provide a device with capability of marking points of interest on cardiac ultrasonically marked leads in such a way as to enable their positive localization and testing of function.

Another object of this invention is to provide a device for making points of interset on cardiac leads sensitive to ultrasound pulses from an echograph, thereby detecting the instant when they are within a scanning plane.

A further object of this invention is to provide cardiac ultrasonically marked leads capable of responding to echoscope ultra sound pulses to give an indication of the lead insulation and lead conductor continuity.

These and other objects will be more readily understood by reference to the following description and accompanying drawing in which FIG. 1 is a partial perspective view of a marked lead with a single transducer.

FIG. 2 is a fragmentary vertical cross section taken on lines 2—2 of FIG. 1.

FIG. 3 is a partial perspective view of a marked lead with a plurality of transducers.

FIG. 4 is a fragmentary cross section taken on lines 4—4 of FIG. 3.

FIG. 5 is a diagram illustrating localization of the transducer in the marked leads.

Figure 6:
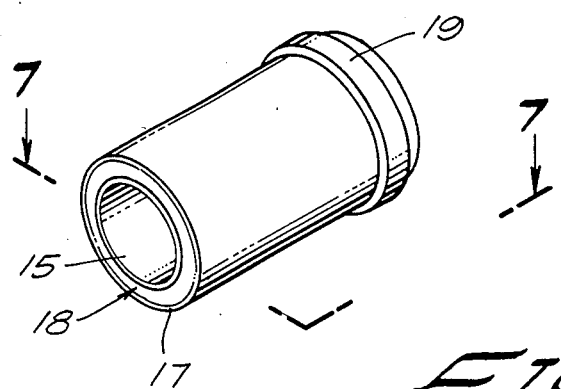
FIG. 6 is a perspective view of a piezoelectric transducer.
Figure 7:
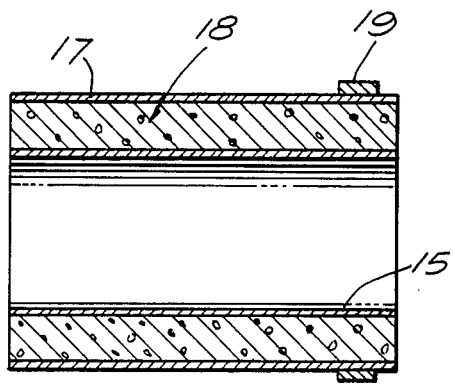

FIG. 7. is a cross section taken on lines 7—7 of FIG. 6.

EXAMPLE 1

In the embodiment of Example 1, the lead 10 has a plastic body 12, an electrode 14, and an electrical conductor 16 which connects the electrode 14 to appropriate lead terminal (not shown). By means of lead terminal, the lead 10 is connected, mechanically and electrically, to the external echo cardiographic marking electronic circuits (not shown).

The lead 10 is also provided with tubiform piezoelectric transducer 18 which is provided with metalized layers 15 and 17, the former on the inner and the latter on the outer surface of transducer tube 18. Metalized layer 17 is provided with a layer of solder material 19 which enables fixation of electrical conductor 20. Electrical connection between electrode 14 and transducer 18 is done by means of tight contact between metalized layer 15 and electrode body 14. The metalized layers 15 and 17 (together with soldering material) represent two tubiform transducer electrodes. The lead 10 is also provided with an ultrasound matching layer 21, which is electrically an insulator. Electrical conductor 16 is normally used for cardiac pacing or electrophysiological purposes and is used here in conjunction with electrical conductor 20 to provide two conductors for transducer 18.

In this way, the transducer 18 can be used as a localization marker in ultrasonic guidance of the medical procedure while at the same time providing a means for detecting any breakage of conductors 16 and 20.

EXAMPLE 2

In the embodiment of Example 2, two marker transducers 22 and 24 are shown with two electrodes 26 and 28, although this embodiment may be modified to include as many transducers and electrodes as necessary.

Electrodes 26 and 28 are principally dome and ring shaped respectively but these shapes may be adapted to conform to use and position along the lead 30 which has a circular cross section.

Transducers 22 and 24 are of the piezoelectric type preferably with a tubular form and are mounted at fixed positions inside the lead plastic body 32 adjacent to the electrodes 26 and 28, to provide electrical connection between transducer electrodes 23 and 25 and electrodes 26 and 28.

The layers or coatings 34 and 36 are of a material and thickness which will have no adverse degrading effect on the performance of the transducers 22 and 24.

Electrical conductors 38 and 40 connect the electrodes 26 and 28 to appropriate lead terminal (not shown), thereby activating both electrodes 26 and 28 and the transducers 22 and 24. Electrical conductors 42 are connected with the other electrodes 27 and 29 of the transducers 22 and 24 and are used in conjunction with electrical conductors 38 and 40 to provide conductors for connection of transducers 22 and 24 to appropriate lead terminal (not shown), thereby to electronic circuitry.

The number of electrode—marker transducers—conductor assemblies may be varied and increased to more than the two of Example 2.

The shape and configuration of the marker transducers provide a wide angle, circular, and nearly omnidirectional sensitivity characteristic, thereby marking the fixed position of the electrodes exactly.

Although we have described our invention in detail with reference to the accompanying drawing illustrating preferred embodiments of our invention, it is understood that numerous changes in the details of construction and arrangements of parts may be made without departing from the spirit and scope of the invention as hereinafter claimed.

We claim:

1. A cardiac ultrasonically marked lead having a distal tip, said lead comprising:
   an elongated plastic body;
   a first electrical conductor;
   an electrode positioned within said plastic body having an exposed electrically conductive surface at the distal tip of said lead and connected to said first electrical conductor, said first conductor leading to a first lead terminal;
   a transducer contained within said plastic body and located adjacent to said electrode, said transducer having an inner and an outer conductive layer, one of said inner and outer layers being in electrical contact with said electrode to provide an electrical connection between said transducer and said electrode;
   a second electrical conductor electrically connected to the other of said inner and outer layers, said second conductor leading to a second lead terminal; and
   an ultrasound matching layer which is electrically an insulator, surrounding said transducer, whereby said transducer provides ultrasonic guidance of medical procedures and detection of breakage of said first electrical conductor and detection of breakage of said ultrasound matching layer.

2. A cardiac ultrasonically marked lead according to claim 1 in which said transducer is tubular in shape, and wherein said inner and outer conductive layers are made of metal.

3. A cardiac ultrasonically marked lead according to claim 1 in which said inner conductive layer is in contact with said electrode to provide an electrical connection between said transducer and said electrode.

4. The method of using a cardiac lead as a localization marker in ultrasonic guidance and as a transmitter of electro-physiological signals for cardiac pacing, said lead including an elongated plastic body, a distal tip, an electrode positioned within said body having an exposed electrically conductive surface at the distal tip of said lead and connected to a first electrical conductor leading to a first lead terminal, a transducer contained within said body and located adjacent said electrode, said transducer having an inner and an outer conductive layer, one of said inner and outer layers being in electrical contact with said electrode to provide an electrical connection between said transducer and said electrode, a second electrical conductor electrically connected to the other of said inner and outer layers, said second conductor leading to a second lead terminal, the method comprising transmitting electrical signals along said second electrical conductor to stimulate transmission and reception of ultrasonic waves by said transducer in order to generate electrical signals for localizing said transducer in an ultrasonic echographic image, and transmitting electrical signals along said first electrical conductor to said electrode in order to stimulate muscle in contact with said exposed electrically conductive surface.

* * * * *